(12) United States Patent
Kelley et al.

(10) Patent No.: US 9,173,952 B2
(45) Date of Patent: *Nov. 3, 2015

(54) MITOCHONDRIAL PENETRATING PEPTIDES AS CARRIERS FOR ANTIMICROBIALS

(75) Inventors: Shana Kelley, Toronto (CA); Mark Pereira, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/700,988

(22) PCT Filed: May 27, 2011

(86) PCT No.: PCT/CA2011/000609
§ 371 (c)(1),
(2), (4) Date: Mar. 8, 2013

(87) PCT Pub. No.: WO2011/150493
PCT Pub. Date: Dec. 8, 2011

(65) Prior Publication Data
US 2013/0157931 A1 Jun. 20, 2013

Related U.S. Application Data

(60) Provisional application No. 61/349,882, filed on May 30, 2010.

(51) Int. Cl.
*A61K 38/08* (2006.01)
*C07K 7/06* (2006.01)
*A61K 47/48* (2006.01)

(52) U.S. Cl.
CPC ............ *A61K 47/48246* (2013.01); *A61K 38/08* (2013.01); *A61K 47/48315* (2013.01); *C07K 7/06* (2013.01)

(58) Field of Classification Search
CPC ............ A61K 47/48246; A61K 38/08; A61K 47/48315; C07K 7/06
See application file for complete search history.

(56) References Cited

U.S. PATENT DOCUMENTS 5,837,218 A * 11/1998 Peers et al. .................... 424/1.69

FOREIGN PATENT DOCUMENTS

WO  WO 2006/049442      5/2006
WO  WO 2007/108749 A1 * 9/2007  ............ C07K 19/00
WO  WO 2009/036092      3/2009

OTHER PUBLICATIONS

Definition of analog and analogue, from http://cancerweb.ncl.ac.uk/cgi-bin/omd?analogue, pp. 1-5, accessed Jul. 7, 2005.*
Property of ANT peptide, p. 1, from STN, accessed Sep. 8, 2014.*
Property of Pep-1, p. 1, from STN, accessed Sep. 8, 2014.*
Property of Tat, p. 1, from STN, accessed Sep. 8, 2014.*
Gray et al, The origin and early evolution of mitochondria, Genome Biology, 2001, 2, pp. 1-5.*
Henriques et al, Cell-penetrating peptides and antimicrobial peptides: how different are they?, Biochem. J., 2006, 399, pp. 1-17.*
Palm et al, Quantitatively determined uptake of cell-penetrating peptides in non-mammalian cells with an evaluation of degradation and antimicrobial effects. Peptides, 2006, 27, pp. 1710-1716.*
Allen and Coombs, "Covalent binding of polycyclic aromatic compounds to mitochondrial and nuclear DNA", *Nature*, 287(5779):244-245, 1980.
Anderson and O'Toole, "Innate and induced resistance mechanisms of bacterial biofilms", *Curr. Top Microbiol Immunol.*, 322:85-105, 2008.
Baba et al., "Construction of *Escherichia coli* K-12 in-frame, single-gene knockout mutants: the Keio collection", *Mol. Syst. Biol.*, 2:2006-2008, 2006.
Barbachyn and Ford, "Oxazolidinone structure-activity relationships leading to linezolid", *Angew Chem Int Ed Engl.*, 42:2010-2031, 2004.
Barnouin et al., "Multidrug resistance protein-mediated transport of chlorambucil and melphalan conjugated to glutathione", *Br. J. Cancer*, 77 :201-209, 1998.
Begleiter et al., "Chlorambucil in Chronic Lymphocytic Leukemia : Mechanism of Action", *Leuk Lymphoma*, 23 :187-201, 1996.
Carreon et al., "Cyanine dye conjugates as probes for live cell imaging", *Bioorganic & Medicinal Chemistry Letters*, 17:5182-5185, 2007.
Cullis et al., "Mechanism and reactivity of chlorambucil and chlorambucil—spermidine conjugate", *Chem. Soc. Perkin Trans.*, 2 :1503-1511, 1995.
Davis et al., "Mitocondrial and Plasma Membrane Potentials Cause Unusual Accumulation and Retention of Rhodamine 123 by Human Breast Adenocarcinoma-derived MCF-7 Cells", *J Biol. Chem*, 260 :13844-13850, 1985.
Ellerby et al., "Anti-cancer activity of targeted pro-apoptotic peptides", *Nature Medicine*, 5(9):1032-1038, 1999.
Espinosa-Mansilla et al., "Kinetic fluorimetric determination of the antineoplastic methotrexate (MTX) in human serum", *J. Pharm. Biomed Anal*, 29:851-858, 2002.
Fan et al., "Cytokine response gene 6 induces p21 and regulates both cell growth and arrest", *Oncogene*, 18:6573-6582, 1999.
Fox and Stover, "Folate-mediated one-carbon metabolism", *Vitam Norm*, 79:1-44, 2008.
Frezza et al., "Organelle isolation : functional mitochondria from mouse liver, muscle and cultured filroblasts", *Nat. Protoc.*, 2 :287-295, 2007.

(Continued)

*Primary Examiner* — Julie Ha
*Assistant Examiner* — Li Ni Komatsu
(74) *Attorney, Agent, or Firm* — Norton Rose Fulbright US LLP

(57) ABSTRACT

There is described herein compounds comprising a mitochondrial penetrating peptide (MPP) conjugated to an antimicrobial, and their method of use.

18 Claims, 18 Drawing Sheets

(56) References Cited

OTHER PUBLICATIONS

Hamilton-Miller, "Antimicrobial activity of 21 anti-neoplastic agents", *Br J. Cancer*, 49:367-369, 1984.
Hanahan and Weinberg, "The Hallmarks of Cancer", *Cell*, 100 :57-70, 2000.
Horton and Kelley, "Engineered Apoptosis-Inducing Peptides with Enhanced Mitochondrial Localization and Potency", *Med. Chem.*, 52:3293-3299, 2009.
Horton et al., "Mitochondria-penetrating peptides", *Chemistry and Biology*, 15(4):375-382, 2008.
Horton et al., "Characterization of a Chlorambucil-Resistant Human Ovarian Carcinoma Cell Line Overexpressing Glutathione S-Transferase m", *Biochem Pharmacol.*, 58 :693-702, 1999.
International Search Report issued in PCT Application No. PCT/CA2011/000609, mailed Sep. 2, 2011.
International Search Report issued in PCT Application No. PCT/CA2011/000610, mailed Sep. 12, 2011.
La Plante and Rybak, "Daptomycin—a novel antibiotic against Gram-positive pathogens", *Expert Opin Pharmacother*, 5:2321-2331, 2004.
Lakshmipathy and Campbell, "The Human DNA Ligase III Gene Encodes Nuclear and Mitochondrial Proteins", *Mol. Cell. Biol.*, 19(5):3869-3876, 1999.
Lowe and Lin, "Apoptosis in Cancer", *Carcinogenesis*, 21(3):485-495, 2000.
Lu et al., "GADD45gamma mediates the activation of the p38 and JNK MAP kinase pathways and cytokine production in effector TH1 cells", *Immunity*, 14(5):583-590, 2001.
Minn et al., "Expression of Bcl-xL Can Confer a Multidrug Resistance Phenotype", *Blood*, 86 :1903-1910, 1995.
Modica-Napolitano and Aprille, "Delocalized lipophilic cations selectively target the mitochondria of carcinoma cells", *Adv. Drug Deliv. Rev.*, 49(1-2):63-70, 2001.
Modica-Napolitano and Aprille, "Basis for the Selective Cytotoxicity of Rhodamine 123", *Cancer Res.*, 47:4361-4365, 1987.
Modica-Napolitano et al., "Selective Damage to Carcinoma Mitochondria by Rhodacyanine MKT-077", *Cancer Res.*, 56 :544-550, 1996.
Muratovska et al., "Targeting large molecules to mitochondria", *Adv. Drug Deliv. Rev.*, 49:189-198, 2001.
Myrberg et al., "Design of a Tumor-Homing Cell-Penetrating Peptide", *Bioconjug. Chem.*, 19 :70-75, 2008.
Pepper et al., "Chlorambucil resistance in B-cell chronic lymphocytic leukaemia is mediated through failed Bax induction and selection of high Bcl-2-expressing subclones", *Br. J. Haematol*, 104 :581-588, 1999.
Pereira and Kelley, "Maximizing the therapeutic window of an antimicrobial drug by imparting mitochondria sequestration in human cells", *Journal of the American Chemical Society*, 133(10):3260-3263, 2011.
Petrini et al., "Reversing of chloramucil resistance by ethacrynic acid in a B-CLL patient", *Br J. Haematol.*, 85 :409-410, 1993.
Pignatello et al., "Lipophilic methotrexate conjugates with antitumor activity", *Eur J. Pharm Sci.*, 10:327-345, 2000.
Preston et al., "Mitochondrial contributions to cancer cell physiology: potential for drug development", *Adv. Drug Deliv. Rev.*, 49:45-61, 2001.
Reed, "Bcl-2 family proteins", *Oncogene*, 17 :3225-3236, 1998.
Santos et al., "Cell Sorting Experiments Link Persistent Mitochondrial DNA Damage with Loss of Mitochondrial Membrane Potential and Apoptotic Cell Death", *J. Biol. Chem.*, 278 :1728-1734, 2003.
Santos et al., "Quantitative PCR-based measurement of nuclear and mitochondrial DNA damage and repair in mammalian cells", *Methods Mol. Biol.*, 314 :183-199, 2006.
Schneider et al., "Virulence gene identification by differential fluorescence induction analysis of *Staphylococcus aureus* gene expression during infection-simulating culture", *Infect Immun.*, 70:1326-1333, 2002.
Singh and Maniccia-Bozzo, "Evidence for lack of mitochondrial DNA repair following cis-dichlorodiammineplatinum treatment", *Cancer Chemother Pharmacol.*, 26(2):97-100, 1990.
Smith and Fornance, "Mammalian DNA damage-inducible genes associated with growth arrest and apoptosis", *Mutat. Res.*, 340(2-3):109-124, 1996.
Sunters et al., "The cytotoxicity, DNA crosslinking ability and DNA sequence selectivity of the aniline mustards melphalan, chlorambucil and 4-[bis(2-chloroethyl)amino] benzoic acid", *Biochem. Pharmacol.*, 44(1):59-64, 1992.
Taubes, "Collateral damage. The rise of resistant C. difficile", *Science*, 321:360, 2008.
Taylor et al., "Apoptosis: controlled demolition at the cellular level", *Nat. Rev. Mol. Cell. Biol.*, 9 :231-241, 2008.
Trombe, "Entry of methotrexate into *Streptococcus pneumonia*: a study on a wild-type strain and a methotrexate resistant mutant", *J Gen Microbiol*, 131:1273-1278, 1985.
Uehara, "Natural product origins of Hsp90 inhibitors", *Current Cancer Drug Targets*, 3(5):325-330, 2003.
Weigel et al., "Genetic analysis of a high-level vancomycin-resistant isolate of *Staphylococcus aureus*", *Science*, 302:1569-1571, 2003.
Wipf et al., "Mitochondrial targeting of selective electron scavengers: synthesis and biological analysis of hemigramicidin-TEMP conjugates", *Journal of the American Chemical Society*, 127(36):12460-12461, 2005.
Wright et al., "Mechanisms of resistance to antibiotics", *Curr. Opin. Chem. Biol.*, 7 :563-569, 2003.
Yang et al., "Role of glutathione and glutathione S-transferase in chlorambucil resistance", *Mol. Pharmacol.*, 41 :625-630, 1992.
Yousif et al., "Mitochondria-penetrating peptides: sequence effects and model cargo transport", *Chembiochem : a European journal of chemical biology*, 10(12):2081-2088, 2009.
Del Gaizo, et al., *Mol Genet Metab.* 80(1-2):170-80, 2003.
Extended European Search Report in European Application No. 11789002.0 mailed Oct. 8, 2013.
Lemeshko, et al., *Archives Biochem Biophys.* 493(2):213-20, 2010.
Luque-Ortega, et al., *The FASEB J.* 22(6):1817-28, 2008.
Anderson et al., "Identification of a de novo thymidylate biosynthesis pathway in mammalian mitochondria," *PNAS* 108(37):15163-15168, 2011.

* cited by examiner

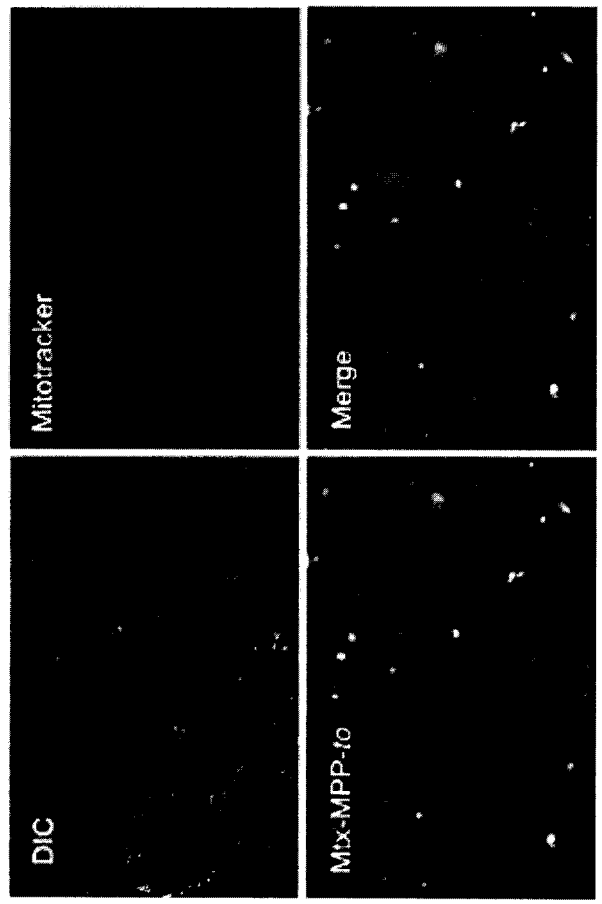

MITOCHONDRIAL PENETRATING PEPTIDES AS CARRIERS FOR ANTIMICROBIALS

CROSS REFERENCE TO RELATED APPLICATIONS

This application is a national phase application under 35 U.S.C. §371 of International Application No. PCT/CA2011/000609 filed May 27, 2011, which claims priority to U.S. Provisional Patent Application Ser. No. 61/349,882 filed May 30, 2010, both of which are incorporated herein by reference in their entirety.

FIELD OF THE INVENTION

This invention relates to cell-permeable peptides that localize to the mitochondria and their use as carriers for antimicrobials.

BACKGROUND OF THE INVENTION

The use of antibacterial agents has become a mainstay in healthcare in the $21^{st}$ century. Since the work of Pasteur and Koch to link a role of bacterial pathogens to disease, we as a society have been driven to develop chemotherapeutics to prevent transmission and to cure microbiological related disease. In recent years, over- and mis-use of these drugs has led to the emergence of resistant pathogens.

Resistance of a bacterium to antibiotics can arise through various mechanisms including modulation of intracellular concentration of the drug through efflux pumps, hindrance of drug influx (e.g. through biofilm formation), enzymatic inactivation, or through modification of the target of the drug.[1,2] Very few classes of antimicrobials have been marketed in the past 46 years (oxazolidinones[3] and lipopeptides[4]). At this pace drug research and discovery may not be able to maintain the tenuous hold that we have on infectious disease. This is particularly evident in the emergence of multi-drug resistant pathogens "superbugs" where health care workers are left with few options for treatment.[5] The Gram-positive *Staphylococcal, Streptococcal, Enterococcal*, and now *Clostridium* pathogens have proven to be a particular challenge in this respect.[6,7]

In small molecule antimicrobial design, the current methods of drug discovery aim to exploit cellular differences between bacterial and human biology to prevent host toxicity from the developed drug. This methodology however limits the effective number of targets that can be exploited for drug design to a few cellular processes. These processes typically include bacterial cell wall biosynthesis, DNA synthesis and protein synthesis, which have been mined considerably for the development of antibiotics since the mid 1940s.

SUMMARY OF THE INVENTION

According to one aspect, there is provided a compound comprising a mitochondrial penetrating peptide (MPP) conjugated to an antimicrobial, preferably an antibacterial.

In another aspect, there is provided the compound described herein for treating infection by a microbe, preferably bacteria, further preferably Gram-positive bacteria.

In another aspect, there is provided a pharmaceutical composition comprising the compound described herein and a pharmaceutically acceptable carrier.

In another aspect, there is provided a library of compounds comprising a plurality of the compounds described herein.

In another aspect, there is provided a method of treating an infection by a microbe, preferably bacteria, further preferably Gram-positive bacteria, in a subject comprising administering to the subject a therapeutically effect amount of the composition described herein.

In another aspect, there is provided a use of the compound described herein in the preparation of a medicament for the treatment of infection by a microbe, preferably bacteria, further preferably Gram-positive bacteria.

In another aspect, there is provided a use of the composition described herein for the treatment of infection by a microbe, preferably bacteria, further preferably Gram-positive bacteria.

In another aspect, there is provided a method of optimizing delivery of an antimicrobial to a microbe, preferably bacteria, further preferably Gram-positive bacteria, comprising conjugating the antimicrobial with a MPP.

BRIEF DESCRIPTION OF THE DRAWINGS

Embodiments of the invention may best be understood by referring to the following description and accompanying drawings. In the description and drawings, like numerals refer to like structures or processes. In the drawings.

DETAILED DESCRIPTION

Figure 1:
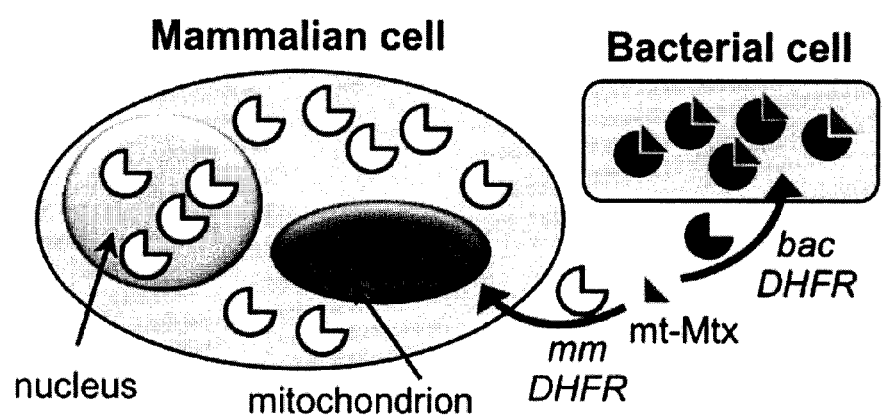
FIG. 1 is a schematic representation of the mechanism of antimicrobial delivery using a mitochondrial targeted peptide-drug conjugate (mt-Mtx) to deliver bacteria-specific toxicity. Conjugation to a mitochondria penetrating peptide increases uptake of small molecule inhibitors into bacteria to reach a protein target. In human cells, however, these molecules are effectively sequestered within mitochondria away from human target reducing toxicity.

In the following description, numerous specific details are set forth to provide a thorough understanding of the invention. However, it is understood that the invention may be practiced without these specific details.

It is described herein that due to shared biological similarities between bacteria and mitochondria, an organelle within human cells, a common peptide transporter can be used for selective uptake within bacteria as well as mitochondria.

According to one aspect, there is provided a compound comprising a mitochondrial penetrating peptide (MPP) conjugated to an antimicrobial, preferably an antibacterial.

As used herein "antimicrobial" means a substance that kills or inhibits the growth of microorganisms, such as bacteria ("antibacterial"), fungi, or protozoans. The antibacterials disclosed herein preferably inhibit or kill Gram-positive bacteria. Antimicrobial drugs can kill microbes (microbicidal) or prevent the growth of microbes (microbistatic). Antimicrobial includes, but is not limited to, the following:

TABLE 1

List of anti-microbial drugs

| Mechanism of Action | Class of Drugs | Examples of potential drugs |
|---|---|---|
| Antimetabolite | Pyrimidine analogues | 5-Fluorouracil Gemcitabine |
|  | Purine analogues | Azathioprine mecaptopurine |
|  | Antifolate | Methotrexate Raltitrexed pemetrexed |
| Inhibition of glycolysis | Hexokinase inhibitor | 2-deoxyglucose 3-bromopyruvate |
|  | Lactate dehydrogenase inhibitor | oxamate |
|  | glucose-6-phosphate dehydrogenase inhibitor | 6-aminonicotinamide |
| Reverse Transcriptase Inhibitor | Antiretroviral | azidothymidine |

In one embodiment, the antimicrobial has a target in human cells that resides in the cytoplasm.

In some embodiments, the antimicrobial is conjugated to the N-terminus of the MPP.

In one embodiment, the compound is Mtx-Fxr3 or MtxA-Fxr3.

The present MPPs preferably possess both positive charge and lipophilic character, properties determined herein to be important for passage across both the plasma and mitochondrial membranes. Thus, MPPs contain cationic and hydrophobic residues to provide a positively charged lipophilic character that facilitates passage through both the plasma and mitochondrial membranes. Cationic amino acids such as lysine (K), arginine (R), aminophenylalanine, and ornithine may be incorporated within the MPPs to provide positive charge, while hydrophobic residues such as phenylalanine (F), cyclohexylalanine ($F_x$), aminooctaarginine (Hex), diphenylalanine ($F_2$) and (1-naphthyl)-L-alanine (Nap), may be incorporated within the MPPs to impart lipophilicity. Although the arrangement of charged and hydrophobic residues within an MPP is not particularly restricted provided the MPP possesses appropriate charge and lipophilicity to pass through the plasma and mitochondrial membranes, the MPPs may comprise alternating charged and hydrophobic residues to increase the level of lipophilicity within the MPP.

MPPs according to the invention may be made using well-established techniques of peptide synthesis, including automated or manual techniques, as one of skill in the art will appreciate.

The length of the present MPPs is not particularly restricted but will generally be of a length suitable for transport across plasma and mitochondrial membranes, either alone or conjugated to another entity such as a biological agent as will be described. Generally, the MPPs will be comprised of 4-20 residues.

The MPPs may include one or more residues modified to impart on the MPP desirable properties, for example, increased intracellular stability. In this regard, for example, the MPPs may include d-stereoisomers, and terminal modifications such as amide termini.

In some embodiments, the MPP can traverse the inner membrane of the mitochondria, preferably in a potential dependent manner.

In some embodiments, the MPP comprises a charge of +3 and a log P value of at least about −1.7.

In other embodiments, the MPP comprises a charge of +5 and a log P value of at least about −2.5.

Preferably, the MPP is any one of SEQ ID NOs. 1-7.

In another aspect, there is provided the compound described herein for treating infection by a microbe, preferably bacteria, further preferably Gram-positive bacteria.

In another aspect, there is provided a pharmaceutical composition comprising the compound described herein and a pharmaceutically acceptable carrier.

In another aspect, there is provided a library of compounds comprising a plurality of the compounds described herein.

In another aspect, there is provided a method of treating an infection by a microbe, preferably bacteria, further preferably Gram-positive bacteria, in a subject comprising administering to the subject a therapeutically effect amount of the composition described herein.

In another aspect, there is provided a use of the compound described herein in the preparation of a medicament for the treatment of infection by a microbe, preferably bacteria, further preferably Gram-positive bacteria.

In another aspect, there is provided a use of the composition described herein for the treatment of infection by a microbe, preferably bacteria, further preferably Gram-positive bacteria.

In another aspect, there is provided a method of optimizing delivery of an antimicrobial to a microbe, preferably bacteria, further preferably Gram-positive bacteria, comprising conjugating the antimicrobial with a MPP.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The following examples are illustrative of various aspects of the invention, and do not limit the broad aspects of the invention as disclosed herein.

Examples

Methods

Cell Culturing Conditions. HeLa cells were cultured in MEM alpha (Invitrogen, Carlsbad) supplemented with 10% (v/v) FBS at 37° C. with 5% $CO_2$. Escherichia coli strain JW5503 from the Keio collection[12] (F−, Δ(araD-araB)567, ΔlacZ4787(:rrnB-3), λ−, ΔtolC732:kan, rph-1, Δ(rhaD-rhaB) 568, hsdR514) was grown on solid LB-agar or in LB liquid media supplemented with 50 μg/mL kanamycin at 37° C. Strains harboring the pCA24N plasmid were additionally grown with chloramphenicol at 20 μg/mL. B. subtilis was grown in LB media. S. aureus and E. faecalis were grown in Trypticase Soy Broth (TSB). S. pneumoniae were grown in TSB+5% defibrinated sheep's blood at 37° C. in an atmosphere of 5% $CO_2$.

Peptide Synthesis & Characterization.

Solid-phase synthesis was performed on Rink amide MBHA resin (0.7 mmol/g, 100-200 mesh) (NovaBiochem) using a Prelude Protein Technologies peptide synthesizer as described previously.[13] Peptides were synthesized on a 25 μmol or 50 μmol scale. Thiazole orange (to) was synthesized as described previously[14] and coupled to peptides using HBTU (4 eq, Protein Technologies, Tucson), HBTU=O-(benzotriazol-1-yl)-N,N,N',N'-tetramethyl-uronium hexafluorophosphate), and DIPEA (8 eq, Sigma-Aldrich, St. Louis), DIPEA=N,N-diisopropylethylamine) in N,N-dimethyl formamide (DMF) overnight. Methotrexate was coupled onto the peptide N-terminus as described.[15] Briefly, Fmoc-L-glutamic acid-α-tert butyl ester was coupled to on resin petide as described above. APA (4 eq) was coupled using N-hydroxybenzotriazole (HOBt, 2 eq), HBTU (4 eq) and DIPEA (8 eq) for 1 hour at room temperature. APA was allowed to activate for 5 minutes prior to addition to resin. MtxA was synthesized by using a Fmoc-L-glutamic acid-γ-tert butyl ester that had been coupled to rink amide resin, and cleaved to yield an amide on the alpha carbon and a deprotected gamma carbon. This product was precipitated in cold ether, confirmed by electrospray ionization mass spectroscopy and used without futher purification. Peptides were deprotected and cleaved from the resin using TFA:triisopropylsilane:$H_2O$ (95:2.5:2.5) and precipitated in cold ether. All peptides were purified to >95% purity by RP-HPLC on a C18 column with a $H_2O$/MeCN gradient in 0.1% TFA and identity confirmed by electrospray ionization mass spectroscopy. Thiazole orange labeled peptides were quantified at 500 nm using an extinction coefficient of 63,000 $M^{-1}$ $cm^{-1}$.[2] Methotrexate conjugted peptides were quantified at 302 nm using the methotrexate extinction coefficient of 22700 $M^{-1}$ $cm^{-1}$. Unlabeled peptides were quatified using a BCA assay (Pierce, Rockford).

Fluorescence Microscopy—Live Cells.

Cells were seeded in 8 well μ-slides (iBidi, Germany) at a density of 25,000 cells per well one day prior to experiments. Peptide incubations (5 μM) were performed for the indicated times in OPTI-MEM (Invitrogen, Carlsbad) without supplementation. Where stated, Mitotracker 633 (Invitrogen, Carlsbad) was added for the last 20 min of the incubation. Cells were then washed twice and imaged using an inverted Zeiss Observer.Z1 microscope. For bacterial imaging, overnight cultures of E. coli JW5503 were subcultured 1/100 and grown to $OD_{600}$ of 0.7 in LB media. Bacteria were treated for 20 min with a peptide concentration of 2 μM in LB media. Cells were washed 2× in PBS and imaged using poly-lysine treated coverslips.

Analysis of Cell Toxicity (HeLa).

HeLa cells were cultured as described above. Cells were seeded in 96-well flat bottom tissue culture plates (Starsted, N.C.) at a density of 1500 cells per well. The culture media was removed and cells were washed with MEM-alpha (minus nucleotides). Concentrated peptide stocks were diluted in MEM-alpha (minus nucleotides)+10% dialyzed FBS and incubated with cells for 72-96 hours. Cellular viability was analyzed after the indicated times using the CCK-8 viability dye (Dojindo, Rockville, Md.) at an absorbance of 450 nm.

Analysis of Toxicity (Bacteria).

Minimum inhibitory concentration (MIC) determinations were performed to characterize the effect of each compound on bacterial growth. Briefly, overnight cultures were subcultured at 1:100 and grown to and $OD_{600}$ of 0.5. Cells were Diluted 1:10000 into fresh media with test compounds. Cells were incubated for 16 hours at 37° C. Growth was monitored at $OD_{600}$. Multi-copy suppression of compound toxicity was accomplished by inducing FolA (DHFR) expression from the pCA24N plasmid with 0.1 mM IPTG prior the incubation with test compounds. Compound toxicity was assessed in LB media for E. coli. For S. aureus B. subtilis, S. pneumonaie, and E. faecalis the defined media Mem-alpha minus nucleotides (Invitrogen, Carlsbad Calif.) was used to control for variability in thymidine content of undefined media. The final dilution into media was at 1:2000 for S. pneumoniae, and E. faecalis. 3% laked horse blood was added to the media for S. pnemoniae.

Mesurement of Mtx Uptake.

Mtx concentrations were determined using a modification of a protocol described previously.[16] HeLa cells. Cells were seeded in a 12-well plate at a density of 100,000 cells per well one day prior to experiments. Cells were treated with indicated amounts of compound in OPTI-MEM for 4 hours at 37° C. Treated cells were washed 2x with PBS and lysed with RIPA buffer. To a 100 µl sample the following was added: 30 µl acetic acid/Na acetate buffer (pH 5.0, 0.5M), 15 µL $KMnO_4$ (1 mM), and 5 µL ascorbic acid (60 µg/mL) and incubated 20 minutes in the dark. 1M Tris buffer pH 7.5 was added and the sample fluoresecence was read in a 96-well plate (ex: 370 nm, em: 460 nm). Protein concentrations were determined using the BCA assay. Bacteria. Cells were subcultured 1/100 from a overnight culture and grown at 37° C. to an $OD_{600}$ of 1 in LB media. 100 µl of these cells were treated with peptide for 20 minutes at 37° C. without shaking. Cells were harvested by centrifugation (13,000 g, 2 min) and washed twice with PBS. Cells were lysed using 0.2% SDS at 100° C. for 5 minutes. An equal volume of $H_2O$ was added and Mtx concentration was analyzed. Mtx concentrations were determined as described above. Uptake in S. aureus and E. faecalis were analysed similarly with the exception that TSB media was used for growth and lysis occurred in 0.4% SDS for 10 minutes at 100° C.

Measurement of Cellular ATP Levels.

HeLa cells were seeded at a density of 50,000 cells per well one day prior to experiments. Cells were treated for 16 hours with compounds Mtx-Fxr3 (16 µM) and Mtx (16 µM) and 1 hour for rotenone (100 nM) in OPTI-MEM media at 37° C. After treatment, cells were washed with PBS, harvested with trypsin/EDTA for 7 min at 37° C. Complete media was added to terminate the reaction and cells were collected by centrifugation (8 min at 700×g) and washed with PBS. Cells were lysed with 40 µl 1% TCA/4 mM EDTA for 20 minutes on ice, followed by 20 µl 1M Tris buffer pH 7.4. ATP levels were assessed using the ATP Bioluminescent Assay Kit (Sigma, Saint Louis Mich.) and a Spectramax M5 plate reader (Molecular Devices, Sunnyvale Calif.).

Measurement of Mitochondrial Membrane Potential.

HeLa cells were seeded in at 6,250 cells per well in 24 well plates. Cells were treated with Mtx-Fxr3 (16 µM) and Mtx (16 µM) for 72 hours in Mem Alpha media with nucleotides and 10% FBS. Carbonyl cyanide 4-(trifluoromethoxy)phenylhydrazone (FCCP) was added at 10 µM for 6 minutes prior to analysis to disrupt the mitochondrial membrane potential. The mitochondrial membrane potential sensitive dye JC-1 (Invitrogen, Carlsbad Calif.) was added at 5 µg/mL for 10 minutes at 37° C. Cells were washed with PBS and harvested as described above. Samples were subsequently analyzed by flow cytometry on a BD FACSCanto flow cytometer (BD Biosciences) with excitation at 488 nm and emmission wavelengths of 530 nm and 585 nm collected. Ratio of these two emmission wavelengths was used to measure changes in mitochondrial membrane potential.

Measurement of Mtx-Fxr3 Elimination from Cells.

Hela cells were incubated with 5 µM of a fluorophore labeled version of Mtx-Fxr3 (Mtx-Fxr3-to) in OPTI-MEM for 45 minutes. After incubation, cells were washed and the OPTI-MEM media was refreshed. Cells were analyzed at the indicated times for retention of the Mtx-Fxr3-to compound by flow cytometry on a BD FACSCanto flow cytometer (BD Biosciences). The excitation wavelength of 488 nm and emmission wavelength of 530 nm was used. A minimum of 10,000 cells were analyzed per sample. The fluorescence median of the live population was used to determine intracellular compound levels.

TABLE 2

List of Peptide Conjugates

| Compound | Peptide Sequence |
| --- | --- |
| Fxr3 | $F_x r F_x r F_x r$ |
| Mtx-Fxr3 | Mtx-$F_x r F_x r F_x r$ |
| MtxA-Fxr3 | MtxA-$F_x r F_x r F_x r$ |
| Mtx-Fxr3-to | Mtx-$F_x r F_x r F_x r$k-to |

$F_x$ = Cyclohexylalanine
r = D configuration of arginine
Mtx = methotrexate
Mtx = modified methotrexate (see FIG. 2)
to = thiazole orange
k = D configuration of lysine Results and Discussion The developed drug delivery system utilizes a peptide transporter to effectively increase the accumulation of antibacterial agents into bacteria, potentiating their antibacterial activity as well as preventing host toxicity by preventing the antibacterial agent from interacting with potential human targets. These goals have been attained though the use of a peptide transporter that shows efficient cellular uptake and specific mitochondrial localization.[8] Mitochondrial penetrating peptides are described in Horton, K. L., Stewart, K. M., Fonseca, S. B., Guo, Q. & Kelley, S. O. Mitochondria-penetrating peptides. *Chem Biol* 15, 375-82 (2008), incorporated herein in its entirety by reference, and includes SEQ ID NOs 1-6 below.

TABLE 3

| Compound | SEQ ID NO. |
| --- | --- |
| $F_x$-r-$F_x$-K-$F_x$-r-$F_x$-K | 1 |
| $F_x$-r-$F_x$-K-F-r-$F_x$-K | 2 |
| Fx-r- $F_x$-K | 3 |
| $F_x$-r- $F_2$-K | 4 |
| $F_x$-r- Nap-K | 5 |
| $F_x$-r- Hex-K | 6 |
| $F_x$-r-$F_x$-r-$F_x$-r | 7 |

$F_x$ = cyclohexylalanine
$F_2$ = diphenyl
Nap = napthyl
Hex = Hexyl

In addition to augmenting the efficacy of small molecules that show bacterial toxicity, through sequestration of the drug within the mitochondrion of human cells prevents the drug from binding to its cytoplasmic target eliminating host (human) toxicity (FIG. 1).

In an aspect, the drug-peptide conjugates described in this invention have two unique features:
1. The peptide domain augments the uptake of drug into bacteria to increase its effective concentration; and
2. The peptide also decreases host cell toxicity by sequestering drugs in the mitochondria away from its cytoplasmic target.

Figure 2A:
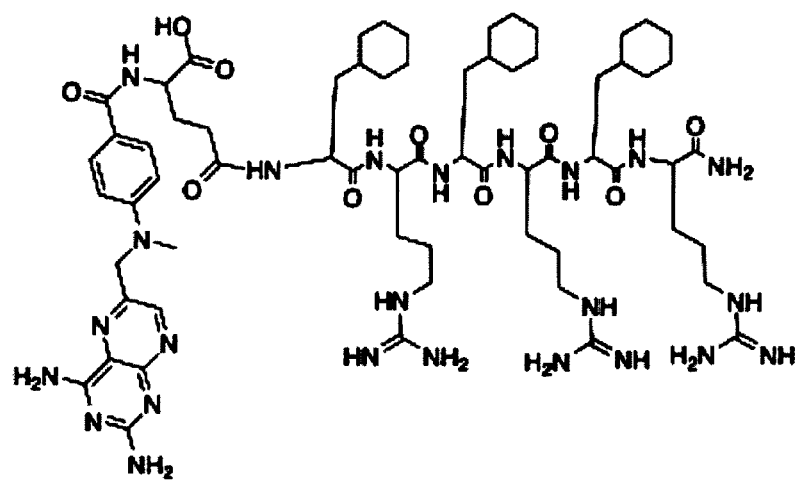
FIG. 2 shows the chemical structure of mitochondrial targeted methotrexate compound. (A) Structure represents direct conjugation of a mitochondria-penetrating peptide (MPP) to methotrexate (Mtx-Fxr3). (B) Structure represents conjugation of an MPP to a version of methotrexate modified to have higher levels of cellular uptake (MtxA-Fxr3).
Figure 2B:
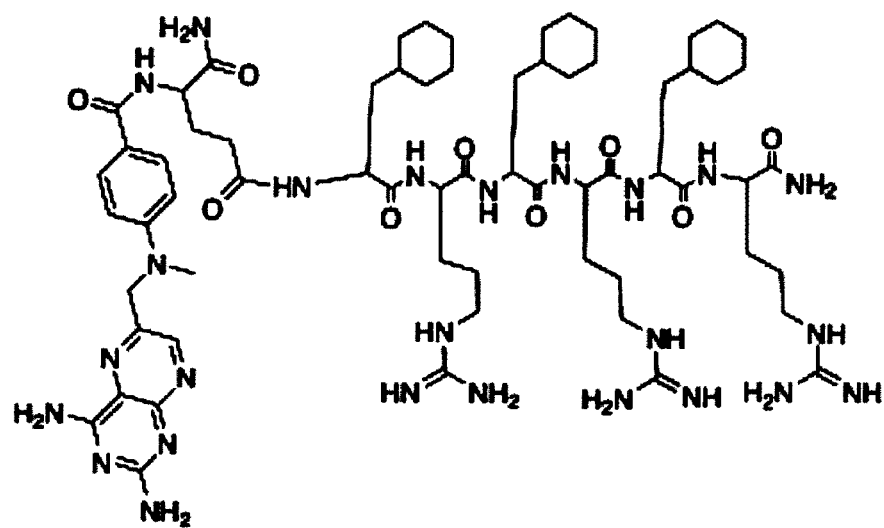

Methotrexate was delivered to each of bacteria and human cells. Methotrexate is an anti-neoplastic agent used in cancer chemotherapy and has appreciable human toxicity. In addition, this molecule only has minimal antibacterial activity against Gram-positive bacteria. These two reasons limit its use to applications that do not include antimicrobial therapy. Two molecules were chemically synthesized to test the utility of MPPs in increasing methotrexate's antimicrobial prospects and are depicted in FIG. 2. Mtx-Fxr3 is a covalent conjugation of a MPP to methotrexate,[9,10] while MtxA-Fxr3 is a modified version engineered to increase cellular uptake. As the problematic pathogens Streptococcus pneumoniae, Enterococcus faecalis (including clinically relevant VRE strains) and Enterococcus faecium show some susceptibility to methotrexate (Hamilton-Miller J. M. T. et al. Br. J. Cancer, 49, 367-369, 1984), enhancing delivery to these organisms will be very clinically relevant.

Figure 3:
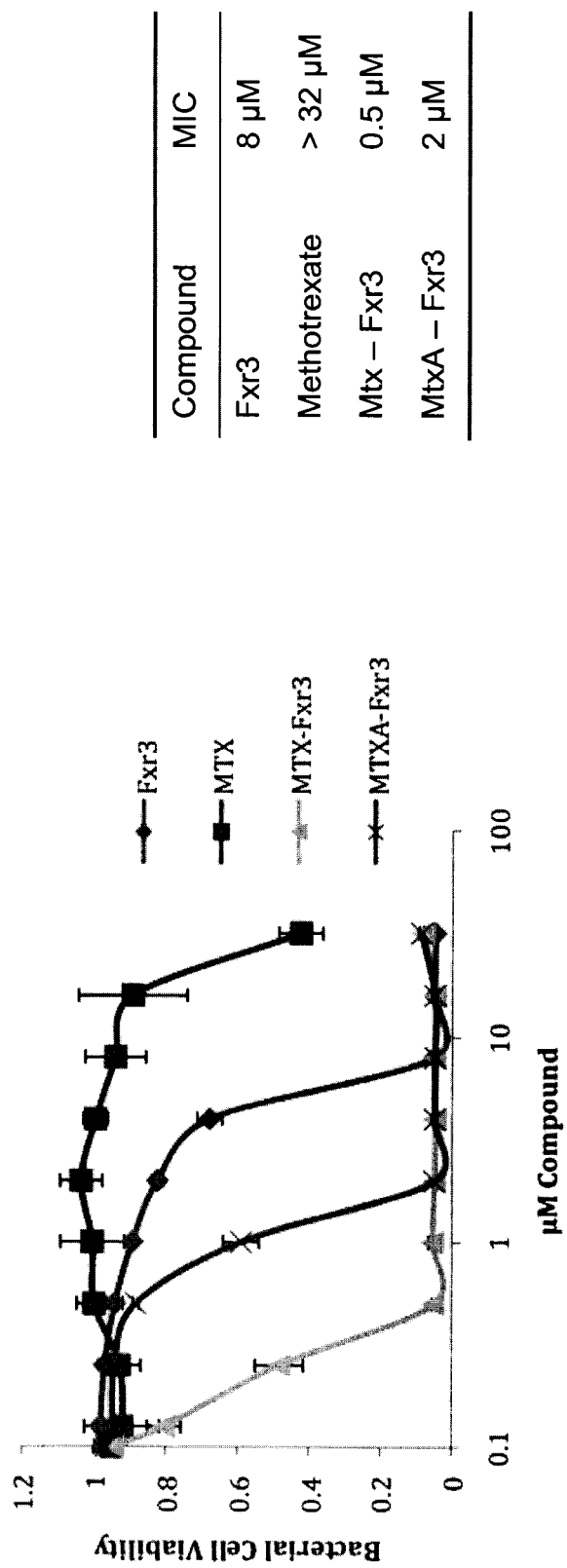
FIG. 3 shows the antimicrobial activity of methotrexate-peptide conjugates. Addition of a MPP to methotrexate increased activity of methotrexate greater than 64 fold. MIC=minimum inhibitory concentration. Experiments conducted in *E. coli* strain JW5503. Mtx: Methotrexate, Fxr3: Mitochondrial Targeting peptide, Mtx-Fxr3: Mitochondrial targeted methotrexate, MtxA-Fxr3: Mitochondrial targeted methotrexate analogue.

These molecules along with methotrexate and the peptide transporter were evaluated for antimicrobial activity in an Escherichia coli strain JW5503 by determining the minimum inhibitory concentration for bacterial growth. Delivery of methotrexate using a mitochondria penetrating peptide potentiated its antimicrobial activity by greater than 64 fold compared to methotrexate alone (FIG. 3). 32 µM methotrexate was not sufficient to inhibit bacterial growth, however 0.5 µM of Mtx-Fxr3 lead to complete inhibition of bacterial growth. Over-expression of the target of methotrexate, the enzyme dihydrofolate reductase (DHFR), abolished the effect of both methotrexate as well as Mtx-Fxr3 (data not shown) suggesting that the antimicrobial affects of Mtx-Fxr3 is due to increased inhibition of DHFR and not simply non-specific toxicity of Mtx-Fxr3. These data demonstrate that utilization of MPPs increase the potency of small molecule antimicrobials.

Figure 4:
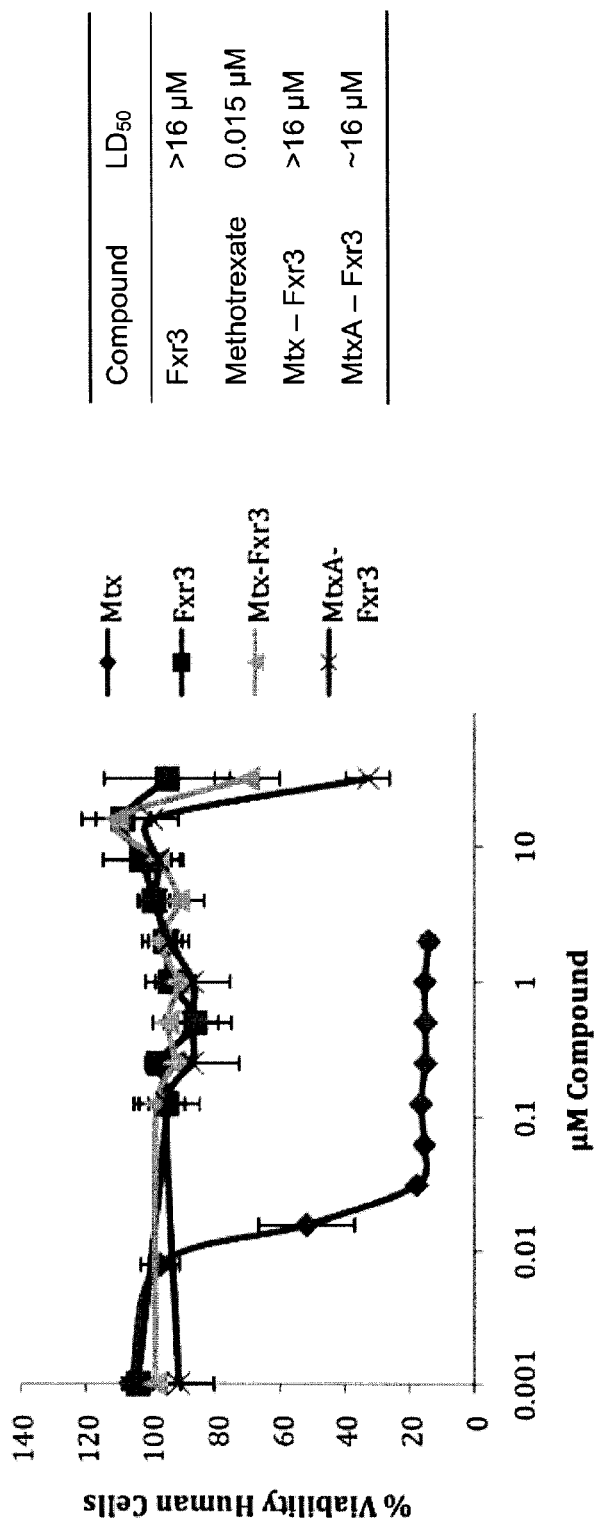
FIG. 4 shows host cell toxicity of methotrexate-peptide conjugates. Attachment of methotrexate to the Fxr3 peptide decreases cellular toxicity by over 1000 fold. $LD_{50}$=Concentration where 50% toxicity is observed. Experiments were conducted in the HeLa cell line. Mtx: Methotrexate, Fxr3: Mitochondrial Targeting peptide, Mtx-Fxr3: Mitochondrial targeted methotrexate, MtxA-Fxr3: Mitochondrial targeted methotrexate analogue.

The target of methotrexate, the enzyme dihydrofolate reductase, is only found in the cytoplasm and nucleus of human cell and not within the mitochondrion.[11] Sequestration of methotrexate within the mitochondrion should abolish the toxicity of the methotrexate. In order to assess host cell toxicity of these compounds, cellular viability of a HeLa cell line after 72-hour incubation with these molecules was evaluated. It was found that through conjugation of methotrexate to an MPP, the toxicity of methotrexate was reduced by 1000-fold (FIG. 4). Mtx had a 50% lethal dose of 0.015 µM while the 50% lethal dose for Mtx-Fxr3 was greater than 16 µM.

Figure 5:
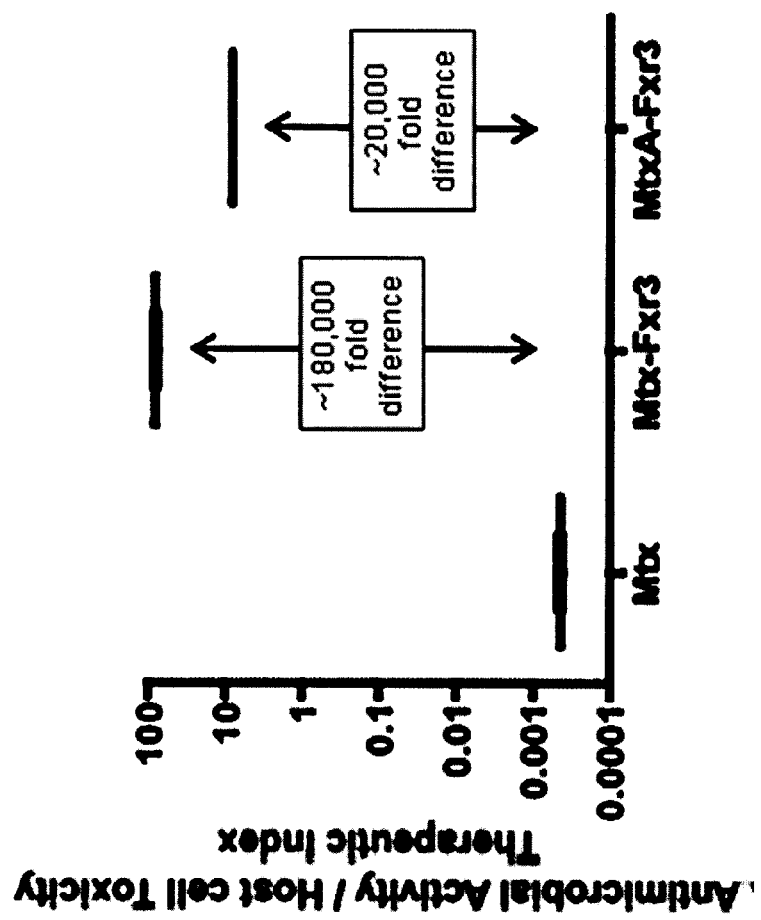
FIG. 5 shows a comparison of antimicrobial prospects of methotrexate and methotrexate-peptide conjugates. The ratio of antimicrobial activity to host cell toxicity (Therapeutic Index) indicates that Mtx-Fxr3 is approximately 180,000 fold more selectively toxic to bacteria than to human cells compared to methotrexate alone. MtxA-Fxr3 is approximately 20,000 fold more selectively toxic to bacteria than human cells compared to methotrexate alone.

Comparing antimicrobial effectiveness and minimization of host cell toxicity together, the addition of an MPP to potentiate uptake of the drug into bacteria and to sequester intracellular drug within mitochondria to reduce toxicity increased the antimicrobial potential of methotrexate by over 180,000 fold (FIG. 5). Similarly, MtxA-Fxr3 had a 20,000 fold increase in Therapeutic Index over Mtx alone. This system can be used for the delivery of other agents that have showed toxicities preventing human use. These data demonstrate that MPPs can be used to decrease the toxicity of antibacterial agents In order to evaluate the intracellular localization of Mtx-Fxr3 in human cells, a fluorescently labelled compound was synthesized Mtx-Fxr3-to. This molecule incorporates the fluorophore thiazole orange. As shown in FIG. 6A, the Mtx-Fxr3 localizes preferentially to the mitochondria of human cells, sequestered away from the cytoplasmic target DHFR.

Figure 6B:
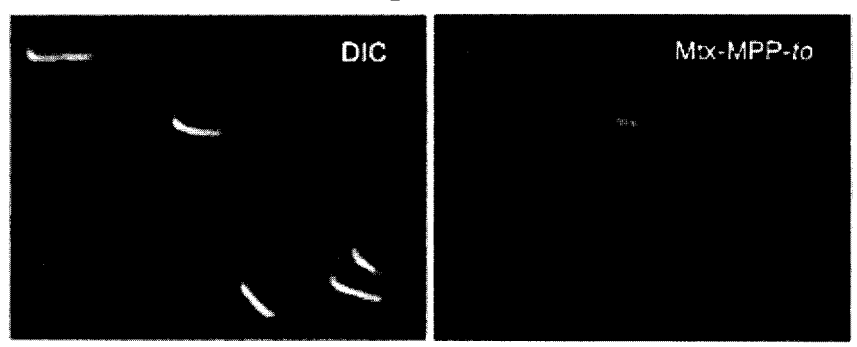
FIG. 6 shows that fluorescently labelled Mtx-Fxr3 localizes to the mitochondria of HeLa cells. (A) Signal from Mtx-Fxr3-to shows intracellular localization in HeLa cells characteristic of mitochondrial accumulation. Mitochondrial staining with commercially available Mitotracker Deep Red 633 shows a similar staining pattern. (B) Mtx-Fxr3-to accumulates within the cytoplasm of *E. coli* JW5503 cells. DIC, differential interference contrast; to, thiazole orange.

In order to assess bacterial localization and characterize the activity of Mtx-Fxr3, Escherichia coli JW5503 that lacks the tolC gene that can cause drug efflux was used as a model strain. The use of this strain presented the opportunity to observe where the drug conjugate would localize once inside a bacterial cell in the absence of competing efflux. When introduced into E. coli JW5503, the drug exhibited a distinct cytoplasmic localization (FIG. 6B).

Figure 7A:
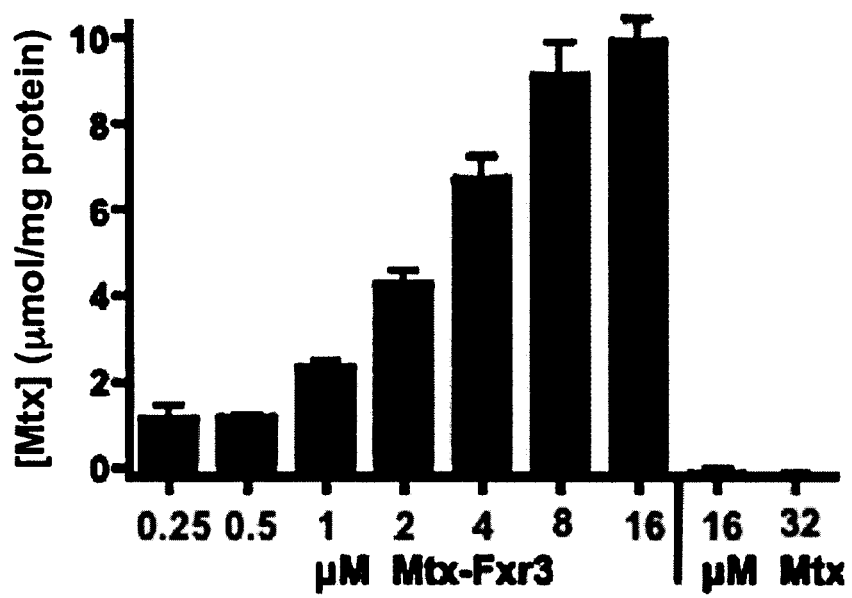
FIG. 7 shows: (A) Relative intracellular concentration of Mtx-Fxr3 in *E. coli* JW5503 and dose-dependent increases in intracellular drug concentrations. With Mix treatment alone, observable accumulation of drug was not detectable. (B) Mtx-Fxr3 accumulates at significantly higher levels within HeLa cells compared to unfunctionalized Mtx.
Figure 7B:
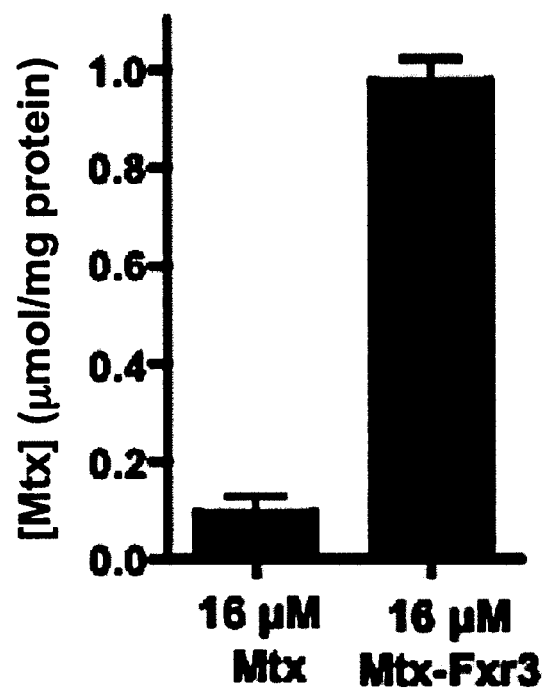

The levels of Mtx in E. coli and mammalian cells were evaluated to confirm that Mtx-Fxr3 accumulates in both cell types. Incubation of Mtx-Fxr3 with E. coli showed a marked dose-dependent increase in peptide concentration. With Mtx, however, no significant accumulation was detectable even at the highest concentrations tested (FIG. 7A), showing that the enhanced potency of the drug in this bacterial strain is derived from peptide-mediated uptake. Similarly, in the mammalian cell line, mitochondrial targeting of Mtx with a peptide resulted in a significant increase in intracellular levels of Mtx (FIG. 7B) when compared to Mtx alone. Toxicity did not result in mammalian cells even when significant levels of Mtx-Fxr3 were present.

Figure 9A:
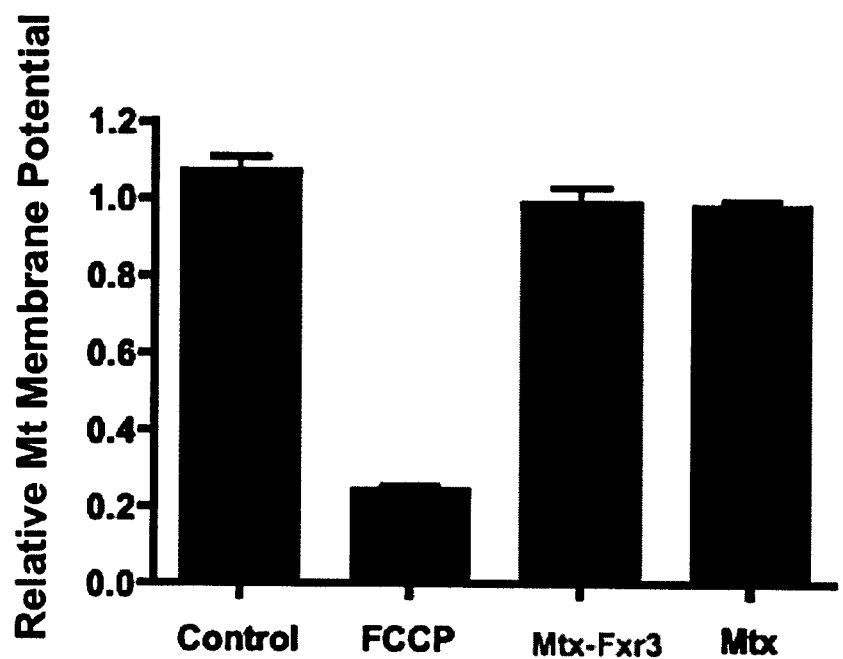
FIG. 9 shows analysis of mitochondrial toxicity of Mtx-Fxr3. (A) Mitochondrial membrane potential was monitored using the mitochondria potential sensitive dye JC-1. Treatment of HeLa cells with Mtx-Fxr3 was found to not perturb the mitochondrial membrane potential. The mitochondrial membrane depolarizer FCCP resulted in a significant decrease in membrane potential. (B) ATP levels were also monitored to assess mitochondrial function. Treatment with Mtx-Fxr3 did not result in a decrease in cellular ATP levels indicating that mitochondrial function was not perturbed. Rotenone, an inhibitor of the electron transport chain, caused a significant decrease in cellular ATP levels. (C) Analysis of Mtx-Fxr3-to levels in cells suggests that this compound is eliminated from HeLa cells in a time dependent manner. Relative compound levels were determined using flow cytometry.
Figure 9B:
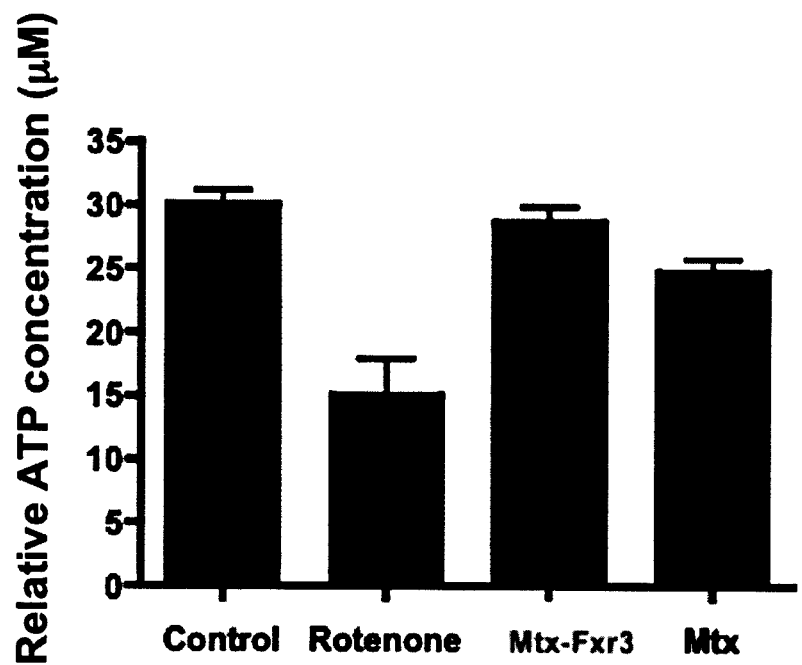
Figure 9C:
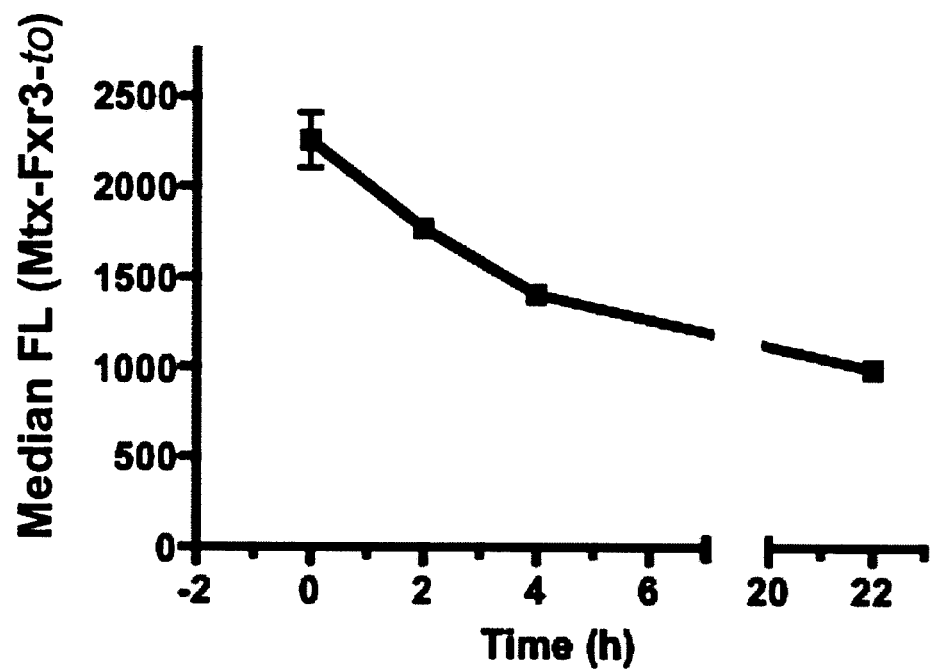

The impact of Mtx-Fxr3 on mitochondrial function and health was assessed. Decreases in mitochondrial membrane potential and decreases in cellular ATP levels are phenotypes associated with mitochondrial toxicity. Treatment of HeLa cells with Mtx-Fxr3 did not affect mitochondrial membrane potential or cellular ATP levels (FIGS. 9A and 9B). Moreover, upon removal of compound from the cell media intracellular levels of the compound decreased in a time dependent manner (FIG. 9C), with >50% of the compound cleared from the cell in 24 hours.

Figure 8A:
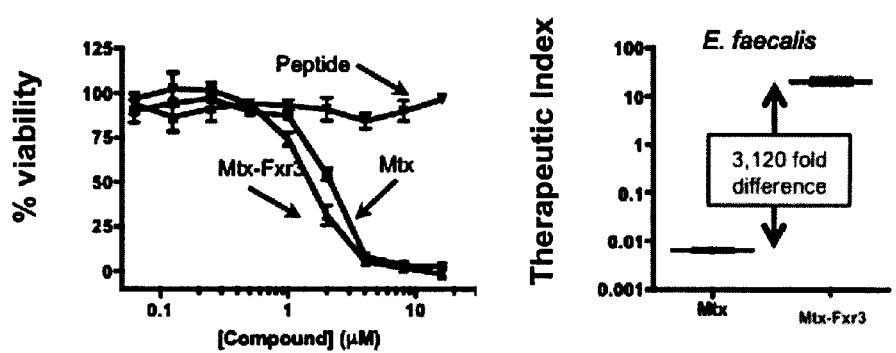
FIG. 8 shows toxicities and therapeutic index calculations for Mtx-Fxr3 and Mtx for Gram-positive pathogens. (A) Activity of Mtx-Fxr3 and Mtx against *E. faecalis* (ATCC 29212). Peptide MIC>16 µM, Mtx-Fxr3 MIC=4 µM, Mtx MIC=4 µM. (B) Activity of Mtx-Fxr3 and Mtx against *B. subtilis*. Peptide MIC>16 µM, Mtx-Fxr3 MIC=8 µM, Mtx MIC>16 µM. (C) Activity of Mtx-Fxr3 and Mtx against *S. pneumoniae* (ATCC 49619). Peptide MIC>16 µM, Mtx-Fxr3 MIC=2 µM, Mtx MIC=0.5 µM. (D) Activity of Mtx-Fxr3 and Mtx against *S. aureus* (ATCC 29213). Peptide MIC>32 µM, Mtx-Fxr3 MIC=16 µM, Mtx MIC>32 µM (E) Activity of Mtx-Fxr3 and Mtx against MRSA (ATCC BAA-1720). Peptide MIC>32 µM, Mtx-Fxr3 MIC=8 µM, Mtx MIC>32 µM. The therapeutic index (ratio of bacterial to human cell toxicity) of Mtx and Mtx-Fxr3 were calculated for each organism. The higher the therapeutic index, the better the compound is as an antimicrobial. The fold differences in the calculated therapeutic indices are indicated.
Figure 8B:
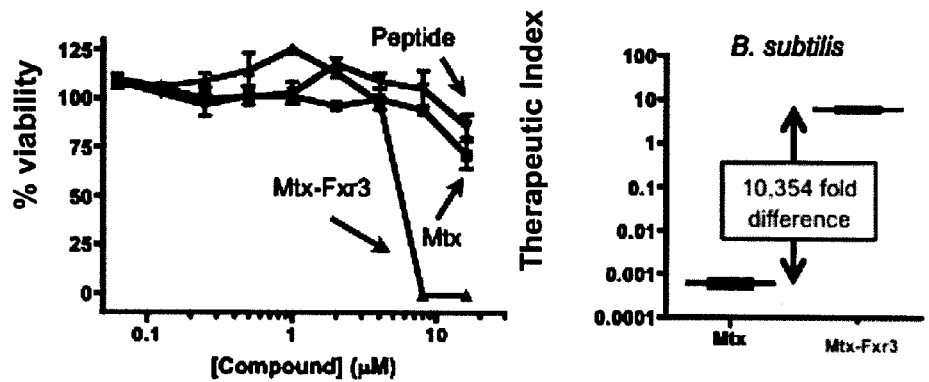
Figure 8C:
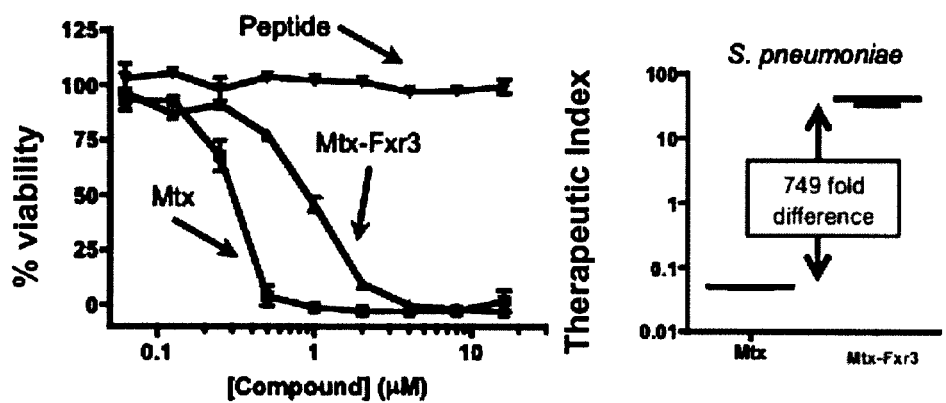
Figure 8D:
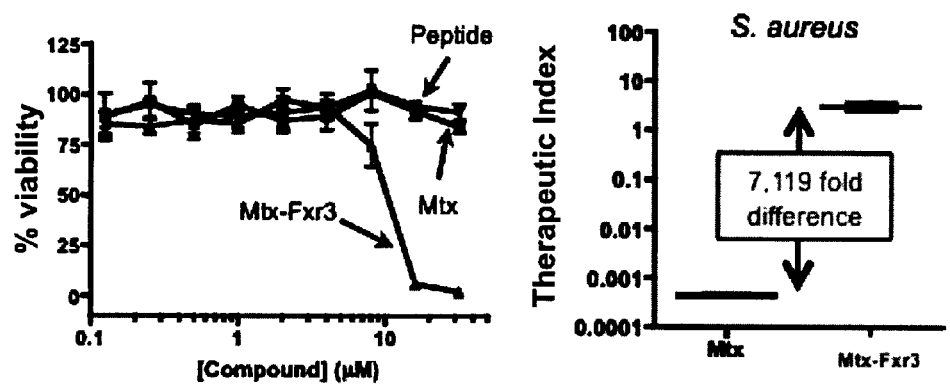
Figure 8E:
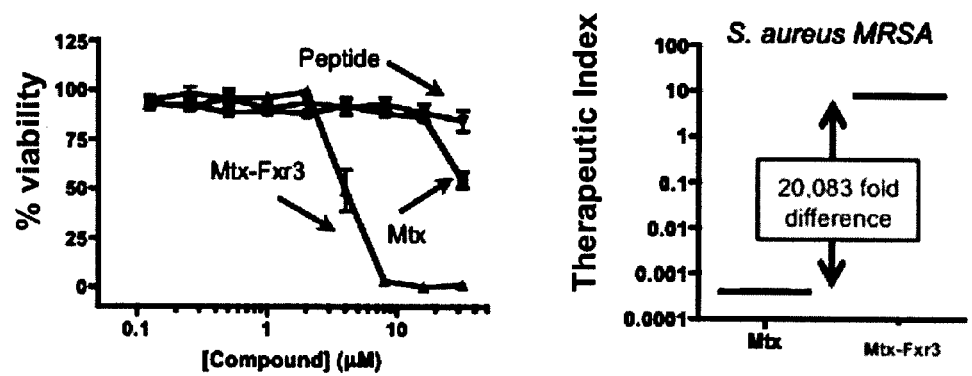

A series of bacterial species, many of which are clinically relevant, were then evaluated. A panel of Gram-positive strains was selected, and activity was observed across a variety of organisms. In Enterococcus faecalis, Mtx-Fxr3 exhibited comparable activity to the parent compound, but given the attenuated activity in human cells, its therapeutic index was >10. This represents a >3000-fold improvement over the parent drug (FIG. 8A). In Bacillus subtilis, Mtx-Fxr3 was significantly more toxic than unmodified Mtx, which produced >10,000 fold improvement in the therapeutic index of the DHFR inhibitor (FIG. 8B). In Streptococcus pneumoniae, Mtx was very active, but the MIC was in the range where significant toxicity occurs in human cells, leading to a therapeutic index <1. For Mtx-Fxr3, the MIC is higher, but the fact that much lower toxicity is observed with this compound in human cells gives the drug a high therapeutic index in S. pneumoniae (FIG. 8C). In Staphylococcus aureus, improved potency is again observed, and the therapeutic index of the drug is improved over 7000-fold (FIG. 8D). Even higher potency was observed for methicillin-resistant S. aureus, and the therapeutic index approached 10 (FIG. 8E).

Figure 10A:
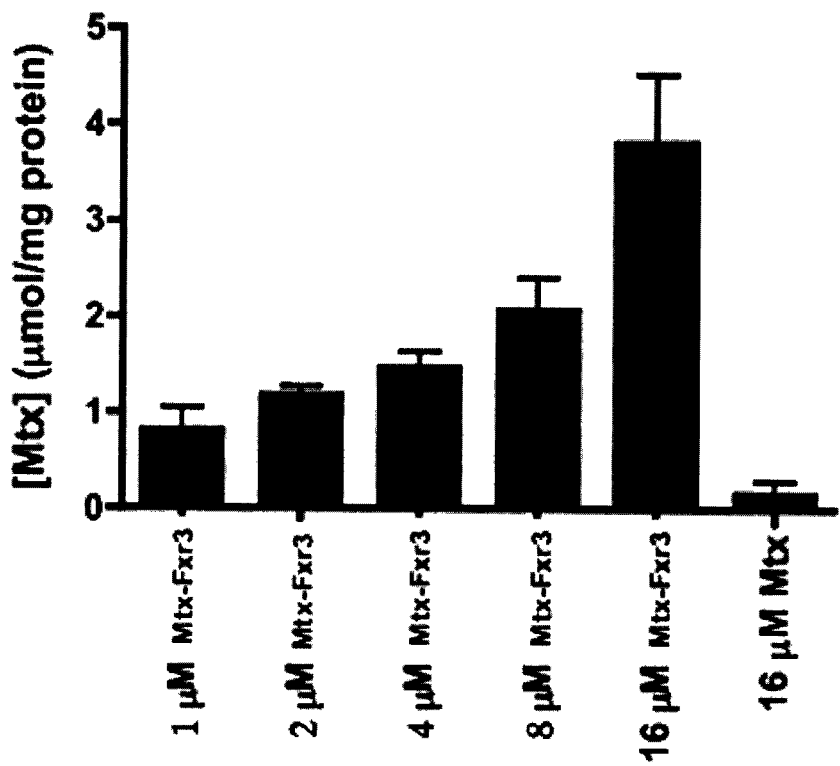
FIG. 10 shows relative intracellular concentration of Mtx-Fxr3 and Mtx in: (A) *S. aureus* and (B) *E. faecalis*. Mtx-Fxr3 accumulated within cells in a dose dependent manner with large increases in uptake at the measured MIC of the compound for that organism. In addition, Mtx-Fxr3 accumulated to a greater extent than Mtx alone.
Figure 10B:
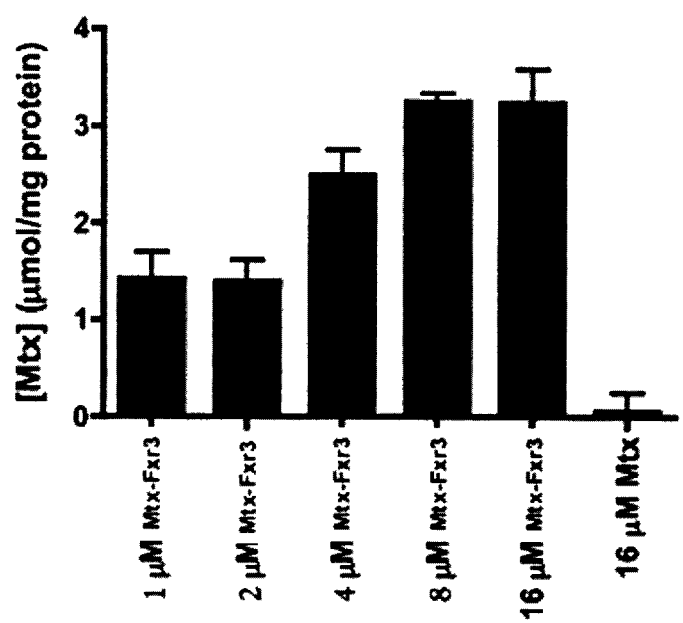

While the peptide appendage did not improve the toxicity of Mtx in all bacterial strains tested, it was effective at improving the potency in E. faecalis, B. subtilis, and S. aureus. Given that higher levels of uptake were observed in E. coli, uptake was evaluated in other types of bacteria. Levels of Mtx and Mtx-Fxr3 were studied in E. faecalis and S. aureus (FIG. 10), and increased uptake for the peptide conjugate over unmodified Mtx was observed in both strains. In addition, the MIC values correlated with the concentration ranges where large increases in uptake occurred.

In summary, by engineering mitochondrial localization into an antibacterial agent, the agent was rendered non-toxic to mammalian cells. Mitochondrial localization was imparted to methotrexate by attaching a mitochondria-penetrating peptide, which sequestered the drug from its enzymatic target. Mtx remained active when conjugated to a mitochondrial targeting vector, and exhibited high levels of activity in the presence of clinically-relevant Gram-positive pathogens. The combination of the antibacterial activity with lowered mammalian cell toxicity produced large improvements in the therapeutic indices for the DHFR inhibitor.

This system can be extended to other small molecule inhibitors where a process essential to the viability of both bacteria and human cells is inhibited provided the human target is not in the mitochondrion.

Two examples of small molecules that would show promise for antimicrobial optimization using this system include 5-fluorouracil and azidothymidine (ziduvane). 5-fluorouracil is a thymidine analogue that inhibits the cytoplasmic target thymidylate synthase, and is used in cancer therapy. As thymidylate synthase is only found in the cytoplasm and the nucleus, conjugation to an MPP shows great promise to repurpose this molecule as an antibacterial agent. Azidothymidine is a therapeutic used in the treatment of HIV that requires enzymatic activation within the cytoplasm of cells to act as an inhibitor of DNA synthesis. Sequestering azidothymidine in the mitochondria will prevent cytoplasmic phosphorylation reactions necessary for activation decreasing the toxicity of the molecule in human cells. Each of these molecules is a promising candidate for conjugation to a mitochondria-penetrating peptide for the basis of antimicrobial design.

Although preferred embodiments of the invention have been described herein, it will be understood by those skilled in the art that variations may be made thereto without departing from the spirit of the invention or the scope of the appended claims. All references disclosed herein are incorporated in the entirety by reference.

REFERENCES

1. Wright, G. D. Mechanisms of resistance to antibiotics. *Curr Opin Chem Biol* 7, 563-9 (2003).
2. Anderson, G. G. & O'Toole, G. A. Innate and induced resistance mechanisms of bacterial biofilms. *Curr Top Microbiol Immunol* 322, 85-105 (2008).
3. Barbachyn, M. R. & Ford, C. W. Oxazolidinone structure-activity relationships leading to linezolid. *Angew Chem Int Ed Engl* 42, 2010-23 (2003).
4. LaPlante, K. L. & Rybak, M. J. Daptomycin—a novel antibiotic against Gram-positive pathogens. *Expert Opin Pharmacother* 5, 2321-31 (2004).
5. Schneider, W. P. et al. Virulence gene identification by differential fluorescence induction analysis of *Staphylococcus aureus* gene expression during infection-simulating culture. *Infect Immun* 70, 1326-33 (2002).
6. Weigel, L. M. et al. Genetic analysis of a high-level vancomycin-resistant isolate of *Staphylococcus aureus*. *Science* 302, 1569-71 (2003).
7. Taubes, G. Collateral damage. The rise of resistant *C. difficile*. *Science* 321, 360 (2008).
8. Horton, K. L., Stewart, K. M., Fonseca, S. B., Guo, Q. & Kelley, S. O. Mitochondria-penetrating peptides. *Chem Biol* 15, 375-82 (2008).
9. Hamilton-Miller, J. M. Antimicrobial activity of 21 antineoplastic agents. *Br J Cancer* 49, 367-9 (1984).
10. Trombe, M. C. Entry of methotrexate into *Streptococcus pneumoniae*: a study on a wild-type strain and a methotrexate resistant mutant. *J Gen Microbiol* 131, 1273-8 (1985).
11. Fox, J. T. & Stover, P. J. Folate-mediated one-carbon metabolism. *Vitam Horm* 79, 1-44 (2008).
12. Baba, T. et al. Construction of *Escherichia coli* K-12 in-frame, single-gene knockout mutants: the Keio collection. *Mol Syst Biol* 2, 2006 0008 (2006).
13. Horton, K. L., Stewart, K. M., Fonseca, S. B., Guo, Q. & Kelley, S. O. Mitochondria-penetrating peptides. *Chem Biol* 15, 375-82 (2008).
14. Carreon, J. R., Stewart, K. M., Mahon, K. P., Jr., Shin, S. & Kelley, S. O. Cyanine dye conjugates as probes for live cell imaging. *Bioorg Med Chem Lett* 17, 5182-5 (2007).
15. Pignatello, R. et al. Lipophilic methotrexate conjugates with antitumor activity. *Eur J Pharm Sci* 10, 237-45 (2000).
16. Espinosa-Mansilla, A., Duran Meras, I., Zamora Madera, A., Pedano, L., & Ferreyra, C. Kinetic fluorimetric determination of the antineoplastic methotrexate (MTX) in human serum. *J. Pharm. Biomed. Anal.* 29, 851-8 (2002).

The invention claimed is:

1. A composition comprising a peptide comprising the amino acid sequence of SEQ ID NO: 7, conjugated to 5-fluorouracil, gemcitabine, azathioprine, mecaptopurine, methotrexate,

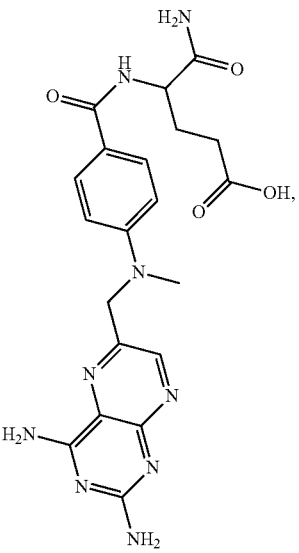

raltitrexed, pemetrexed, 2-deoxyglucose, 3-bromopyruvate, oxamate or 6-aminonicotinamide.

2. The composition of claim 1, wherein the peptide is conjugated to 5-fluorouracil.

3. The composition of claim 1, wherein the peptide is conjugated to gemcitabine.

4. The composition of claim 1, wherein the peptide is conjugated to azathioprine.

5. The composition of claim 1, wherein the peptide is conjugated to methotrexate.

6. The composition of claim 1, wherein the peptide is conjugated to 2-deoxyglucose.

7. The composition of claim 1, wherein the peptide is conjugated to mecaptopurine.

8. The composition of claim 1, wherein the peptide consists of the amino acid sequence of SEQ ID NO:7.

9. The composition of claim 1, wherein the 5-fluorouracil, gemcitabine, azathioprine, mecaptopurine, methotrexate,

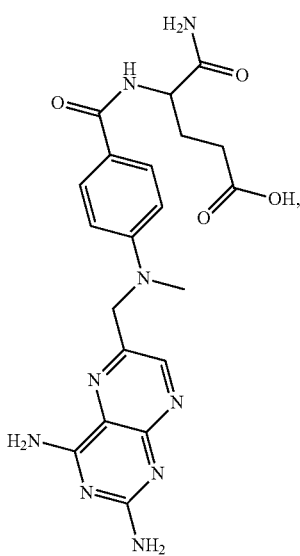

raltitrexed, pemetrexed, 2-deoxyglucose, 3-bromopyruvate, oxamate or 6-aminonicotinamide is conjugated to the N-terminus of the peptide.

10. The composition of claim 1, wherein the peptide consists of the amino acid sequence of SEQ ID NO:7, conjugated to either methotrexate or

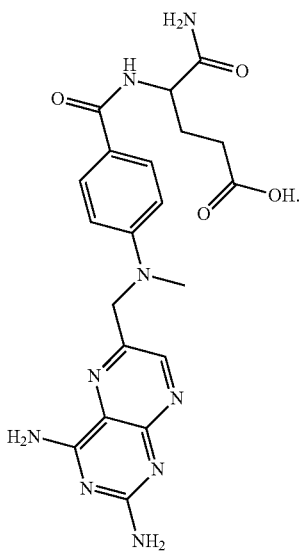 [SMILES: CN(Cc1cnc2nc(N)nc(N)c2n1)c1ccc(C(=O)NC(CCC(=O)O)C(N)=O)cc1]

11. The composition of claim 1, wherein the peptide is conjugated to

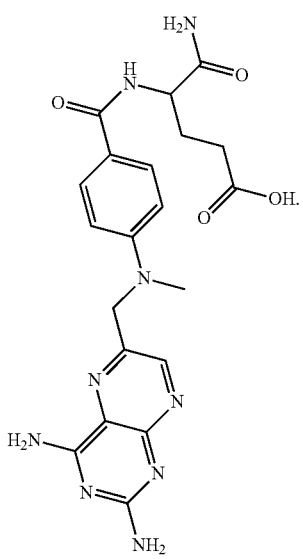 [SMILES: CN(Cc1cnc2nc(N)nc(N)c2n1)c1ccc(C(=O)NC(CCC(=O)O)C(N)=O)cc1]

12. The composition of claim 1, wherein the peptide is conjugated to raltitrexed.

13. The composition of claim 1, wherein the peptide is conjugated to pemetrexed.

14. The composition of claim 1, wherein the peptide is conjugated to 3-bromopyruvate.

15. The composition of claim 1, wherein the peptide is conjugated to oxamate.

16. The composition of claim 1, wherein the peptide is conjugated to 6-aminonicotinamide.

17. A pharmaceutical composition comprising the composition of claim 1 and a pharmaceutically acceptable carrier.

18. A peptide consisting of the amino acid sequence of SEQ ID NO:7.

\* \* \* \* \*

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residues 1, 3, 5 and 7 are cyclohexylalanine
<220> FEATURE:
<221> NAME/KEY: misc_feature
<223> OTHER INFORMATION: residues 2 and 6 are d-arginine

<400> SEQUENCE: 1

Xaa Xaa Xaa Lys Xaa Xaa Xaa Lys
1               5
```

-continued

```
<210> SEQ ID NO 2
<211> LENGTH: 8
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residues 1, 3 and 7 are cyclohexylalanine
<220> FEATURE:
<221> NAME/KEY: misc_feature
<223> OTHER INFORMATION: residues 2 and 6 are d-arginine

<400> SEQUENCE: 2

Xaa Xaa Xaa Lys Phe Xaa Xaa Lys
1               5

<210> SEQ ID NO 3
<211> LENGTH: 4
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residues 1 and 3 are cyclohexylalanine
<220> FEATURE:
<221> NAME/KEY: misc_feature
<223> OTHER INFORMATION: residue 2 is d-arginine

<400> SEQUENCE: 3

Xaa Xaa Xaa Lys
1

<210> SEQ ID NO 4
<211> LENGTH: 4
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residue 1 is cyclohexylalanine
<220> FEATURE:
<221> NAME/KEY: misc_feature
<223> OTHER INFORMATION: residue 3 is diphenyl
<220> FEATURE:
<221> NAME/KEY: misc_feature
<223> OTHER INFORMATION: residue 2 is d-arginine

<400> SEQUENCE: 4

Xaa Xaa Xaa Lys
1

<210> SEQ ID NO 5
<211> LENGTH: 4
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residue 1 is cyclohexylalanine
<220> FEATURE:
<221> NAME/KEY: misc_feature
<223> OTHER INFORMATION: residue 3 is napthyl
<220> FEATURE:
<221> NAME/KEY: misc_feature
<223> OTHER INFORMATION: residue 2 is d-arginine

<400> SEQUENCE: 5

Xaa Xaa Xaa Lys
```

```
<210> SEQ ID NO 6
<211> LENGTH: 4
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residue 1 is cyclohexylalanine
<220> FEATURE:
<221> NAME/KEY: misc_feature
<223> OTHER INFORMATION: residue 3 is hexyl
<220> FEATURE:
<221> NAME/KEY: misc_feature
<223> OTHER INFORMATION: residue 2 is d-arginine

<400> SEQUENCE: 6

Xaa Xaa Xaa Lys
1

<210> SEQ ID NO 7
<211> LENGTH: 6
<212> TYPE: PRT
<213> ORGANISM: Artificial Sequence
<220> FEATURE:
<223> OTHER INFORMATION: mitochondrial penetrating peptide
<220> FEATURE:
<221> NAME/KEY: misc_feature
<223> OTHER INFORMATION: residues 2, 4 and 6 are d-arginine
<220> FEATURE:
<221> NAME/KEY: misc_feature
<223> OTHER INFORMATION: residues 1, 3 and 5 are cyclohexylalanine

<400> SEQUENCE: 7

Xaa Xaa Xaa Xaa Xaa Xaa
1               5
```